United States Patent [19]

Fabre et al.

[11] 4,124,596
[45] Nov. 7, 1978

[54] THIENOTHIENYLCARBONYL-PHENYLALKANOIC ACIDS AND DERIVATIVES THEREOF

[75] Inventors: Jean-Louis Fabre, Paris; Daniel Farge, Thiais; Claude James, Paris, all of France

[73] Assignee: Rhone-Poulenc Industries, Paris, France

[21] Appl. No.: 763,141

[22] Filed: Jan. 27, 1977

[30] Foreign Application Priority Data

Jan. 29, 1976 [FR] France .................................. 76 02378
Jul. 20, 1976 [FR] France .................................. 76 22066
Dec. 16, 1976 [FR] France .................................. 76 37858

[51] Int. Cl.² ...................... C07D 333/24; A01N 9/00
[52] U.S. Cl. .............................. 260/332.2 A; 424/275
[58] Field of Search .................... 260/332.2 A

[56] References Cited

FOREIGN PATENT DOCUMENTS 2,211,214 9/1972 Fed. Rep. of Germany ... 260/332.2 A

Primary Examiner—A. Siegel

Attorney, Agent, or Firm—Stevens, Davis, Miller & Mosher

[57] ABSTRACT

Compounds of the formula:

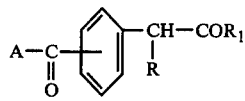

wherein R represents hydrogen or an alkyl radical, $R_1$ represents a hydroxy, amino or alkoxy radical or an alkylamino or dialkylamino group, the various alkyl radicals and the alkoxy radical being optionally substituted by a dialkylamino group, the alkyl radicals of the said dialkylamino groups optionally being linked together to form a heterocyclyl radical with 5 or 6 atoms in the ring, and A represents the thieno[2,3-b]thien-2-yl or thieno[3,2-b]thien-2-yl radical, the A—CO— grouping being attached to the 3- or 4-position of the phenyl ring, have been found to possess useful pharmacological properties and are particularly active as analgesics, antipyretics, agents for inhibiting platelet aggregation and as anti-inflammatory agents.

13 Claims, No Drawings

THIENOTHIENYLCARBONYL-PHENYLALKANOIC ACIDS AND DERIVATIVES THEREOF

This invention relates to new therapeutically useful thienothienylcarbonyl-phenylalkanoic acids and derivatives thereof, to processes for their preparation and pharmaceutical compositions containing them.

The new thienothienylcarbonyl-phenylalkanoic acids and derivatives thereof of the present invention are those compounds of the general formula:

I

[wherein R represents a hydrogen atom or an alkyl radical, $R_1$ represents a hydroxy, amino or alkoxy radical, or an alkylamino or dialkylamino group, the various alkyl radicals and the alkoxy radical being optionally substituted by a dialkylamino group, it being understood that in the definitions of R and $R_1$ above the alkyl radicals and the alkoxy radical contain from 1 to 4 carbon atoms and that the alkyl radicals of the dialkylamino groups may be linked together to form a heterocyclyl radical with 5 or 6 atoms in the ring which may optionally contain another hetero-atom selected from nitrogen, oxygen and sulphur (e.g. piperidino, morpholino or piperazin-1-yl), and the symbol A represents the thieno[2,3-b]thien-2-yl or thieno[3,2-b]thien-2-yl radical, the A—CO— grouping being attached to the 3- or 4-position of the phenyl ring] and — when appropriate — pharmaceutically acceptable salts thereof, viz. when $R_1$ represents the hydroxy radical their pharmaceutically acceptable metal salts, e.g. alkali metal and alkaline earth metal salts, ammonium salts and addition salts with nitrogen-containing bases, and when $R_1$ represents a group containing basic nitrogen their pharmaceutically acceptable acid addition salts.

According to a feature of the invention, the compounds of general formula I, wherein R and A—CO— are as hereinbefore defined and $R_1$ represents the hydroxy radical, are prepared by the process which comprises hydrolyzing a nitrile of the general formula:

II (wherein R is as hereinbefore defined and the grouping A—CO— as defined above is attached to the 3- or 4-position of the phenyl ring) by methods known per se for the conversion of a nitrile to the corresponding acid without affecting the rest of the molecule. By the term "methods known per se" as used in this specification is meant methods heretofore used or described in the chemical literature.

It is particularly advantageous to heat the nitrile of general formula II under reflux in water in the presence or absence of an organic solvent such as methanol, ethanol or ethylene glycol, and in the presence of a base such as sodium hydroxide or potassium hydroxide, or in the presence of an acid such as hydrochloric acid.

The nitriles of general formula II can be prepared by reacting a compound of the general formula:

III (wherein R is as hereinbefore defined and the chloroformyl radical is attached to the 3- or 4-position of the phenyl ring) with a heterocyclic compound of the general formula:

A — H   IV (wherein A is as hereinbefore defined) in accordance with a Friedel and Crafts reaction.

Generally, the reaction is carried out in an inert organic solvent, such as methylene chloride, in the presence of a catalyst, such as aluminium chloride, at a temperature between 0° C. and the reflux temperature of the reaction mixture.

The nitriles of general formula II wherein R represents an alkyl radical can also be obtained by alkylation, in the presence of an alkaline agent, of a nitrile of general formula II wherein R represents a hydrogen atom.

The reaction is generally effected by the action of an alkyl halide or sulphate, the alkyl moiety of which contains 1 to 4 carbon atoms, in the presence of a base such as an alkali metal hydroxide, hydride or amide, in a polar, aprotic, basic solvent. More particularly, the reaction is carried out by the action of an alkyl iodide or sulphate, either in the presence of potassium hydroxide in a solvent such as N-methyl-2-pyrrolidone or hexamethylphosphotriamide at a temperature between 10° and 50° C., or in the presence of sodamide in an organic solvent such as hexamethylphosphotriamide of dimethylformamide at a temperature between 0° and 50° C., or in the presence of an aqueous solution of sodium hydroxide and a catalyst selected from tetraalkylphosphonium, tetraalkylammonium, tetraalkylarsonium, tetraalkyl phosphonium and arsonium double salts, or mixed alkyl-aryl phosphonium and arsonium salts, at a temperature between 20° and 40° C.

The compounds of general formula III can be prepared according to any of the usual methods for the preparation of acid chlorides from the corresponding acids, that is to say from acids of the general formula:

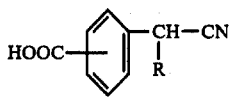
V (wherein R is as hereinbefore defined and the carboxy radical is attached to the 3- or 4-position of the phenyl ring) according to a method disclosed in Belgian Patent Specification No. 792218. Preferably, thionyl chloride is reacted with an acid of general formula V in an organic solvent such as carbon tetrachloride, chloroform or benzene, at the reflux temperature of the reaction mixture. It is not absolutely necessary to purify the acid of the general formula V in order to prepare the chloride of general formula III.

The acids of general formula V, wherein R is as hereinbefore defined and the carboxy radical is attached to the 3-position of the phenyl ring, can be obtained by reacting a nitrile of the general formula:

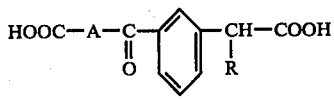

(wherein R is as hereinbefore defined) with 2-chlorobenzoic acid, in accordance with the method described by E. R. Biehl, J. Org. Chem., 31, 602 (1966).

The acid of general formula V, wherein R represents a hydrogen atom and the carboxy radical is attached to the 4-position of the phenyl ring, can be prepared by application of the process described by W. Mellinghoff, Chem. Ber., 22, 3213 (1889).

The acids of general formula V, wherein R represents an alkyl radical containing 1 to 4 carbon atoms and the carboxy radical is attached to the 4-position of the phenyl ring, can be obtained in accordance with the method described by E. R. Biehl et al., J. Org. Chem., 34, 500, (1969).

Thieno[2,3-b]thiophene and thieno[3,2-b]thiophene can be prepared according to the method described by A. Bugge, Acta. Chem. Scand., 22, 63 (1968).

According to another feature of the invention, the compounds of general formula I, wherein R represents an alkyl radical and $R_1$ represents the hydroxy radical, are prepared by the process which comprises the alkylation, in the presence of an alkaline agent, of the carbon atom attached to the phenyl ring of a corresponding phenylacetic acid derivative of general formula I wherein R represents a hydrogen atom and $R_1$ represents the hydroxy radical, followed by saponification of the ester formed during the reaction. The alkylation is generally effected by the action of an alkyl halide or sulphate, the alkyl moiety of which contains from 1 to 4 carbon atoms, in the presence of a base such as an alkali metal hydroxide, hydride or amide, in a polar, aprotic, basic solvent, followed by saponification of the ester and liberation of the acid by acidification.

The conditions hereinbefore described for the preparation of nitriles of general formula II, wherein R represents an alkyl radical, from a nitrile of general formula II wherein R represents a hydrogen atom are generally appropriate.

Saponification of the intermediate ester is generally carried out by means of potassium hydroxide at a temperature of about 25° C.

According to a still further feature of the invention, the compounds of general formula I, wherein R is as hereinbefore defined, $R_1$ represents the hydroxy radical and the A—CO— grouping is attached to the 3-position of the phenyl ring, are prepared by partial decarboxylation of a di-acid of the general formula:

VII wherein R is as hereinbefore defined and the HOOC—A— grouping represents the 5-carboxy-(thieno[2,3-b]thien-2-yl) or the 5-carboxy-(thieno[3,2-b]thien-2-yl) radical.

Generally the decarboxylation is carried out in the presence of copper at a temperature between 160° and 290° C. in an organic solvent such as diphenyl ether or quinoline.

The di-acids of general formula VII can be obtained by saponification of a di-ester of the general formula:

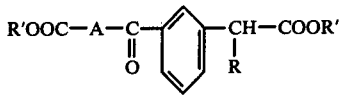

VIII wherein R is as hereinbefore defined, the grouping R'OOC—A— represents a 5-alkoxycarbonyl-(thieno[2,3-b]thien-2-yl) or a 5-alkoxycarbonyl-(thieno[3,2-b]thien-2-yl) radical, and R' represents the methyl or ethyl radical.

The saponification is advantageously carried out by the action of sodium hydroxide or potassium hydroxide in an aqueous alcoholic medium, for example in a mixture of ethanol and water, at a temperature between 20° C. and the reflux temperature of the reaction mixture.

The di-esters of general formula VIII can be obtained by the action, in an anhydrous acid medium, of an alcohol of the general formula:

R'—OH    IX (wherein R' is as hereinbefore defined) on a nitrile of the general formula:

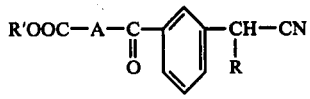

X (wherein R and the grouping R'OOC—A— are as hereinbefore defined) by applying a method known per se for the conversion of a nitrile to an ester without affecting the rest of the molecule.

The reaction is generally carried out in the presence of anhydrous hydrogen chloride in an organic solvent, such as methylene chloride, at a temperature between 0° and 10° C., and then the hydrochloride of the imino-ether formed is hydrolysed.

The nitriles of general formula X can be prepared by reacting a compound of general formula III (wherein the Cl—CO— group is attached to the 3-position of the phenyl ring) with a thienothiophene derivative of the general formula:

R'OOC—AH    XI (wherein the grouping R'OOC—A— is as hereinbefore defined) in accordance with a Friedel and Crafts reaction.

The reaction is generally carried out under the conditions hereinbefore described for preparing a nitrile of general formula II by the action of a compound of general formula III on thieno[2,3-b]thiophene or on thieno[3,2-b]thiophene, i.e. a heterocyclic compound of formula IV.

The compounds of general formula XI can be prepared from an acid of the general formula:

HOOC—AH    XII (wherein HOOC—A— is as hereinbefore defined) by applying a method known per se for the obtention of an ester from an acid without affecting the rest of the molecule.

It is particularly advantageous to carry out a direct esterification of an acid of general formula XII by means of an alcohol of general formula IX, in an anhydrous acid medium, for example in the presence of anhydrous hydrogen chloride, or to react an alkyl halide with an alkali metal salt or a quaternary ammonium salt of an acid of general formula XII in an organic solvent such as benzene, toluene, acetone, diethyl ether or chloroform, working at a temperature between 20° C. and the reflux temperature of the reaction mixture. To prepare the methyl ether, it is also possible to react diazomethane with an acid of the general formula XII at a temperature between −20° and 4° C., working in an organic solvent such as diethyl ether.

Thieno[2,3-b]thiophene-2-carboxylic acid and thieno[3,2-b]thiophene-2-carboxylic acid can be prepared according to the method described by A. Bugge, Acta. Chem. Scand., 22, 63 (1968).

According to another feature of the invention, the compounds of general formula I, wherein R and A are as hereinbefore defined, $R_1$ represents the hydroxy radical and the A—CO— radical is attached to the 4-position of the phenyl ring, are obtained from an ester of the general formula:

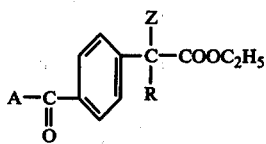

XIII (wherein R and A are as hereinbefore defined and Z represents a cyano, ethoxycarbonyl or acetyl radical) according to methods known per se for the hydrolysis and decarboxylation of cyanoacetic, malonic and acetylacetic esters, without affecting the rest of the molecule.

This reaction is preferably carried out by heating an ester of general formula XIII in water or in an organic solvent such as ethanol, in the presence of a base such as potassium hydroxide or sodium hydroxide, or of an acid such as hydrochloric acid, at a temperature between 20° C. and the reflux temperature of the reaction mixture.

The esters of general formula XIII can be prepared by reacting an alkali metal derivative, optionally prepared in situ, of a compound of the general formula:

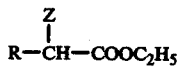

XIV (wherein R and Z are as hereinbefore defined) with a halogeno compound of the general formula:

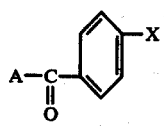

XV wherein A is as hereinbefore defined and X represents a halogen atom.

The reaction is generally effected with the sodium derivative of the compound of general formula XIV in an organic solvent such as hexamethylphosphotriamide, at a temperature between 20° and 150° C.

The halogeno compounds of general formula XV can be obtained by decarboxylation of an acid of the general formula:

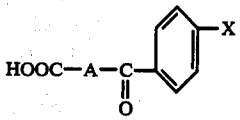

XVI wherein HOOC—A— and X are as hereinbefore defined.

The decarboxylation is generally carried out in the presence of copper, in a solvent such as quinoline or diphenyl ether, at a temperature between 160° C. and the reflux temperature of the reaction mixture.

The acids of general formula XVI can be prepared from an ester of the general formula:

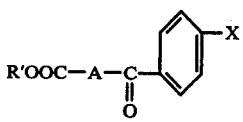

XVII (wherein the grouping R'OOC—A— and X are as hereinbefore defined) by any method known per se for obtaining an acid from an ester, without affecting the rest of the molecule.

The conditions hereinbefore described for the preparation of a di-acid of general formula VII from an ester of general formula VIII are generally applicable.

The esters of general formula XVII can be prepared by the action of a corresponding 4-halogenobenzoyl chloride on a thienothiophene derivative of the general formula XI in accordance with a Friedel and Crafts reaction.

The reaction is generally carried out under the conditions hereinbefore described for the preparation of a nitrile of general formula II by the action of a compound of general formula III on thieno[2,3-b]thiophene or on thieno[3,2-b]thiophene.

4-Fluorobenzoyl chloride can be prepared according to the method described by F. Fichter et al., Helv. Chim. Acta., 16, 1156 (1933).

4-Chlorobenzoyl chloride, 4-bromobenzoyl chloride and 4-iodobenzoyl chloride can be prepared according to the method described by H. Meyer, Monatsh. Chem., 22, 777 (1901).

According to another feature of the invention, the compounds of general formula I, wherein R is as hereinbefore defined and $R_1$ represents an alkoxy radical optionally substituted by a dialkylamino group, the alkoxy and alkyl radicals containing from 1 to 4 carbon atoms and the alkyl radicals of the dialkylamino group optionally being linked together to form a heterocyclyl radical with 5 or 6 atoms in the ring which may optionally contain another hetero-atom selected from nitrogen, oxygen and sulphur, and the A—CO— grouping (A being as hereinbefore defined) is attached to the 3- or 4-position of the phenyl ring, are prepared from a corresponding compound of general formula I, wherein $R_1$ represents the hydroxy radical, by any method known per se for converting an acid to an ester of an alcohol of the general formula:

$R_1$OH  XVIII (wherein $R_{1'}$ represents an alkyl radical optionally substituted by a dialkylamino group, the alkyl radicals containing from 1 to 4 carbon atoms and the alkyl radicals of the dialkylamino group optionally being linked together to form a heterocylyl radical with 5 or 6 atoms in the ring which may optionally contain another hetero-atom selected from nitrogen, oxygen and sulphur) without affecting the rest of the molecule.

It is particularly advantageous to react a halide of the alcohol of general formula XVIII, viz. the product in which the hydroxy radical is replaced by a halogen atom, with an alkali metal salt or an ammonium salt of the acid of general formula I. The reaction is generally carried out by the action of the chloride on the sodium salt of the acid of the general formula I in a solvent such as dimethylformamide, at a temperature of about 25° C. If it is desired to prepare the methyl ester, it is also possible to react diazomethane with the acid of general formula I.

According to another feature of the invention, the compounds of general formula I, wherein R is as hereinbefore defined, $R_1$ represents an amino radical or an alkylamino or dialkylamino group, the alkyl radicals of which optionally being substituted by a dialkylamino group (it being understood that the alkyl radicals of the dialkylamino group(s) can optionally be linked together to form a heterocyclyl radical with 5 or 6 atoms in the ring which optionally contain another hetero-atom selected from nitrogen, oxygen and sulphur) and the A—CO— grouping (A being as hereinbefore defined) is attached to the 3- or 4-position of the phenyl ring, are prepared from a corresponding acid of general formula I wherein $R_1$ represents the hydroxy radical, or optionally from the chloride of such an acid, by any method known per se for obtaining an amide from an acid or from its chloride without affecting the rest of the molecule.

Generally the amides are prepared by the action of an amine on the acid of the general formula I, in the presence of N,N'-carbonyldiimidazole or dicyclohexylcarbodiimide, at a temperature of about 25° C., or by the action of an amine on the chloride of the acid of general formula I at a temperature between 20° and 50° C. Advantageously, the reaction is effected in an organic solvent such as diethyl ether, tetrahydrofuran, dimethylformamide or chloroform.

The compounds of general formula I when there is present one or more centres of chirality may exist in the form of optically active isomers. The present invention includes within its scope all such optically active isomers and mixtures thereof, and more particularly the racemic form.

Optically active isomers of general formula I can be obtained by resolving a racemic form of the product by formation of an optically active salt and successive crystallisations. This resolution is generally carried out by means of D-α-phenylethylamine or L-α-phenylethylamine, depending on the isomer which it is desired to obtain.

The compounds of general formula I can be converted, where appropriate, into metal salts or addition salts with a nitrogen-containing base, by the application of methods known per se, or they can, where appropriate, be converted into acid addition salts with acids. The metal salts and salts of nitrogen-containing bases can be obtained by the action of, for example, an alkali metal base or an alkaline earth metal base, of ammonia or of a nitrogen-containing base on an acid of general formula I wherein $R_1$ represents the hydroxy radical, in an appropriate solvent such as an alcohol, a ketone, an ether or water; the salt which forms is precipitated, optionally after concentration of its solution, and is removed by filtration or decantation. Acid addition salts of a compound of general formula I wherein $R_1$ represents a group containing basic nitrogen can be obtained by reaction of the base with an acid in an organic solvent such as an alcohol, a ketone, an ether or a chlorinated hydrocarbon.

Of particular interest are the compounds of general formula I wherein R and the grouping A—CO— are as hereinbefore defined, and $R_1$ represents the hydroxy radical, or an alkoxy radical substituted by a dialkylamino group, e.g. —OCH$_2$CH$_2$N(C$_2$H$_5$)$_2$, or an alkylamino group substituted on the alkyl radical by a dialkylamino group, e.g. —NH—CH$_2$CH$_2$N(CH$_3$)$_2$. Amongst such compounds those of the general formula:

XIX (wherein R and A are as hereinbefore defined) are of outstanding interest, and especially 2-{3-(thieno[2,3-b]thien-2-yl)carbonyl-phenyl}propionic acid and 2-{3-(thieno-[3,2-b]thien-2-yl)carbonyl-phenyl}propionic acid.

The new compounds of general formula I, and — when appropriate — their optically active isomers and their salts, exhibit useful pharmacological properties; they are particularly active as analgesics, antipyretics, agents for inhibiting platelet aggregation and as anti-inflammatory agents. They are of low toxicity.

The analgesic and antipyretic activities manifest themselves in rats at doses of between 40 and 100 mg/kg animal body weight administered orally, according to the technique of L. O. Randall and J. J. Selitto [Arch. Int. Pharmacodyn., 111, 409, (1957)] modified by K. F. Swingle et al. [Proc. Soc. Exp., Biol. Med., 137, 536, (1971)], and at doses of between 30 and 100 mg/kg animal body weight administered orally, according to the technique of J. J. Loux et al. [Toxicol. Appl. Pharmacol., 22, 674 (1972)].

The inhibitory activity on platelet aggregation manifests itself in rabbits at doses of between 2 and 30 mg/kg animal body weight administered orally, according to a technique similar to that of Born et al. [J. Physiol., 168, 178, (1963)], and at doses of between 3 and 100 mg/kg animal body weight administered orally, according to a technique similar to that of Silver et al. [Science, 183, 1085, (1974)].

The anti-inflammatory activity manifests itself in rats at doses of between 10 and 150 mg/kg animal body weight administered orally, according to the technique of K. F. Benitz and L. M. Hall [Arch. Int. Pharmacodyn., 144, 185, (1963)].

In mice, the acute toxicity is between 300 and 900 mg/kg animal body weight or greater than 900 mg/kg animal body weight administered orally.

For therapeutic purposes the compounds of general formula I can be employed as such or — when appropriate— in the form of pharmaceutically acceptable salts, that is to say salts which are non-toxic to the animal organism at therapeutic doses of the salts.

Examples of suitable pharmaceutically acceptable salts are the salts with alkali metals (such as the potassium, sodium or lithium salt) or with alkaline earth metals, the ammonium salt, salts with nitrogen-containing bases (such as ethanolamine and lysine), and acid addition salts with inorganic or organic acids (such as hydrochlorides, sulphates, nitrates, phosphates, acetates, propionates, succinates, benzoates, fumarates, maleates, theophylline-acetates, salicylates, phenolphthalinates and methylene-bis-β-hydroxynaphthoates).

The following non-limitative Examples illustrate the preparation of compounds of the present invention.

EXAMPLE 1

2-{3-(Thieno[2,3-b]thien-2-yl)carbonyl-phenyl}propionitrile (34.7 g) is suspended in a mixture (122 cc) of equal parts of ethylene glycol and 6N aqueous sodium hydroxide solution. The suspension obtained is then heated for 21 hours under reflux. After cooling to 25° C., the reaction mixture is diluted with water (610 cc), decolourizing charcoal (0.2 g) is added and the mixture is filtered. The filtrate is poured dropwise, with stirring, into 2N hydrochloric acid (200 cc), the temperature being maintained at 24°-25° C. Stirring is continued for 1 hour. The resulting precipitate is filtered off, washed three times with distilled water (total 750 cc) and dried under reduced pressure (20 mm Hg) at 25° C. After grinding the partially dried precipitate, the drying is completed under reduced pressure (1 mm Hg) at 25° C. for 24 hours. The crude product obtained (27.5 g), melting at 90° C., is dissolved in methanol (107 cc), decolourizing charcoal (0.2 g) is added, and the solution is filtered. The filtration residue is washed three times with methanol (total 32 cc). The combined organic solutions are neutralized with a 3.42N methanolic solution of sodium methoxide (53.5 cc), decolourizing charcoal (0.5 g) is added, and the solutions are filtered and evaporated. The residue obtained, to which a product (2.2 g) obtained in the same way is added, is recrystallized from methyl ethyl ketone (321 cc). After 16 hours at 5° C., the resulting crystals are filtered off, washed once with methyl ethyl ketone (50 cc), then three times with diethyl ether (total 150 cc), dried under reduced pressure (1 mm Hg) at 60° C. for 24 hours, and then kept in an atmosphere controlled to 58% humidity until constant weight is achieved. In this way, the sodium salt of 2-{3-(thieno[2,3-b]thien-2-yl)carbonyl-phenyl}propionic acid (8.5 g), melting at 285° C., is obtained.

2-{3-(Thieno[2,3-b]thien-2-yl)carbonyl-phenyl}propionitrile can be prepared in the following way:

A mixture of thieno[2,3-b]thiophene (23.8 g) and 2-(3-chloroformyl-phenyl)propionitrile (29.6 g) is added dropwise to a suspension of anhydrous aluminium chloride (50 g) in methylene chloride (425 cc). After 16 hours at 25° C., the reaction mixture is heated under reflux for 40 minutes and then, after cooling, distilled water (600 cc) and 12N hydrochloric acid (50 cc) are added. The organic phase is decanted and the aqueous phase is extracted twice with methylene chloride (total 200 cc). The combined methylene chloride solutions are washed three times with distilled water (total 1500 cc), and then stirred with 5N aqueous sodium hydroxide solution (50 cc) for 2 hours at 25° C. The organic phase is decanted, washed four times with distilled water (total 2000 cc) and dried over anhydrous sodium sulphate, decolourizing charcoal (5 g) is added, and the organic phase is filtered and evaporated. The residue obtained (43.6 g) is chromatographed on a column (4.8 cm diameter, 47 cm height) containing silica gel (410 g). Elution is carried out with methylene chloride (total 1500 cc). The first fraction (500 cc) is discarded, whilst the two following fractions are combined and concentrated to dryness. 2-{3-(Thieno[2,3-b]thien-2-yl)carbonylphenyl}propionitrile (16.9 g) is obtained in the form of an oil. Rf = 0.60 (silica gel chromatographic plate; solvent: methylene chloride).

Thieno[2,3-b]thiophene can be prepared according to the method of A. Bugge, Acta. Chem. Scand., 22, 63 (1968).

2-(3-Chloroformyl-phenyl)propionitrile can be prepared according to the method described in Belgian Patent Specification No. 792218.

EXAMPLE 2

A homogeneous mixture of 3-(5-carboxythieno[2,3-b]thien-2-yl)carbonyl-phenylacetic acid (24 g), copper powder (4 g) and Fontainebleau sand (100 g) is heated at 290° C. for 1 hour. After cooling, the reaction mixture is washed five times with methylene chloride (total 350 cc). The combined methylene chloride phases are extracted five times with a 10% (w/v) aqueous solution of sodium carbonate (total 400 cc). The combined alkaline liquors are stirred with decolourizing charcoal (1 g), filtered, acidified to pH 1 by addition of a 12N concentrated aqueous solution of hydrogen chloride, and extracted three times with methylene chloride (total 300 cc). The combined methylene chloride solutions are dried over anhydrous sodium sulphate and evaporated. The residue (17.3 g) is dissolved in boiling acetonitrile (50 cc) and the solution is filtered. After cooling for 1 hour at 4° C., the resulting crystals are filtered off, washed three times with iced acetonitrile (total 15 cc) and dried under reduced pressure (20 mm Hg) at a temperature of about 20° C., in the presence of potassium hydroxide pellets used as a dehydrating agent. Crude 3-(thieno[2,3-b]thien-2-yl)carbonyl-phenylacetic acid (10.6 g), melting at 121° C., is thus obtained.

The crude 3-(thieno[2,3-b]thien-2-yl)carbonylphenylacetic acid (22.6 g) is dissolved in boiling acetonitrile (80 cc). Decolourizing charcoal (0.5 g) is added to the solution and the solution is filtered. The filtrate is cooled for 1 hour at 4° C., and the resulting crystals are filtered off, washed three times with iced acetonitrile (total 15 cc), and dried under reduced pressure (20 mm Hg) at a temperature of about 20° C. in the presence of potassium hydroxide pellets. Pure 3-(thieno[2,3-b]thien-2-yl)carbonyl-phenylacetic acid (14.6 g), melting at 126° C., is thus obtained.

3-(5-Carboxy-thieno[2,3-b]thien-2-yl)carbonylphenylacetic acid can be prepared in the following way:

Methyl (5-methoxycarbonyl-thieno[2,3-b]thien-2-yl)carbonyl-phenyl acetate (67.5 g), in suspension in a solution of potassium hydroxide pellets (49.4 g) in distilled water (300 cc) and ethanol (800 cc), is first stirred for 17 hours at a temperature of about 20° C., and then stirred for 3 hours at 45°-50° C. The volume of the reaction mixture is then reduced by half by distillation under reduced pressure (30 mm Hg) at 45°-50° C., and the residue is diluted with distilled water (1400 cc). The solution obtained is stirred with decolourizing charcoal (2 g), and filtered. The filtrate is added dropwise to a 5N aqueous solution of hydrochloric acid (500 cc), cooled in an ice bath, the rate of addition being regulated in such a way that the temperature of the mixture remains below 10° C. After standing for 17 hours at 4° C., the resulting crystals are filtered off, washed three times with distilled water (total 300 cc), then three times with iced ethanol (total 90 cc), and dried in air at 40° C. After grinding of the partially dried crystals in a mortar, the drying is completed under reduced pressure (20 mm Hg) at a temperature of about 20° C. in the presence of potassium hydroxide pellets. Crude 3-(5-carboxy-thieno[2,3-b]thien-2-yl)carbonyl-phenylacetic acid (67 g), melting at 283° C., is thus obtained.

Methyl 3-(5-methoxycarbonyl-thieno[2,3-b]thien-2-yl)carbonyl-phenyl acetate can be prepared in the following way:

3-(5-Methoxycarbonyl-thieno[2,3-b]thien-2-yl)carbonyl-phenylacetonitrile (47.2 g) is dissolved in a mixture of methanol (290 cc) and methylene chloride (575 cc). The solution, cooled to −4° C., is saturated with hydrogen chloride by bubbling through a brisk stream of anhydrous hydrogen chloride for 6 hours and is then kept at 0° C. for 17 hours. Distilled water (400 cc) is then added to the reaction mixture which is heated progressively, whilst distilling the methylene chloride, until the temperature of the mixture reaches 70° C., a temperature which is maintained for 1½ hours. After the addition of distilled water (250 cc) and cooling for 1 hour at 4° C., the resulting crystals are filtered off, washed three times with distilled water (total 300 cc) and dried in air. Methyl 3-(5-methoxycarbonyl-thieno[2,3-b]thien-2-yl)carbonyl-phenyl acetate (49.5 g), melting at 152° C., is thus obtained.

3-(5-Methoxycarbonyl-thieno[2,3-b]thien-2-yl)carbonyl-phenylacetonitrile can be prepared in the following way:

Anhydrous aluminium chloride (167.5 g) is added in small portions over a period of 1½ hours to a mixture of methyl (thieno[2,3-b]thiophene-2-carboxylate (49.5 g) and 3-chloroformyl-phenylacetonitrile (44.8 g) in methylene chloride (1250 cc) at 20°–30° C. The reaction mixture is stirred for 17 hours at a temperature of about 20° C., then hydrolysed, with care, by the slow addition of an N aqueous solution of hydrogen chloride (500 cc), the internal temperature being kept at about 20° C. by external cooling with an ice bath. The aqueous phase is decanted off and extracted three times with methylene chloride (total 600 cc). The combined methylene chloride solutions are washed three times with distilled water (total 240 cc), dried over anhydrous sodium sulphate in the presence of decolourizing charcoal (2 g), filtered and evaporated. The residue is taken up in boiling acetonitrile (250 cc). After cooling for 1 hour at 4° C., the resulting crystals are filtered off, washed three times with iced acetonitrile (total 60 cc), and dried under reduced pressure (20 mm Hg) at a temperature of about 20° C. in the presence of potassium hydroxide pellets. 3-(5-Methoxycarbonyl-thieno[2,3-b]thien-2-yl)carbonyl-phenylacetonitrile (74.7 g), melting at 184° C., is thus obtained.

3-Chloroformyl-phenylacetonitrile can be prepared according to the method described in Belgian Patent Specification No. 792218.

EXAMPLE 3

2-{3-(5-Carboxy-thieno[2,3-b]thien-2-yl)carbonyl-phenyl}propionic acid (14 g), copper powder (1.5 g) and copper turnings (1.5 g) are suspended in diphenyl ether (60 cc) and heated at 250° C. for 30 minutes. After cooling, the reaction mixture is diluted with methylene chloride (100 cc), decolourizing charcoal (1 g) is added and the mixture is filtered. The filtrate is extracted three times with a 10% (w/v) aqueous solution of sodium carbonate (total 150 cc), and then washed twice with distilled water (total 100 cc). The combined aqueous phases are acidified to pH 1 by the addition of 12N concentrated hydrochloric acid and extracted four times with methylene chloride (total 200 cc). The combined methylene chloride solutions are washed three times with distilled water (total 90 cc), dried over anhydrous sodium sulphate and evaporated. Crude 2-{3-(thieno[2,3-b]thien-2-yl)carbonyl-phenyl}propionic acid (7.5 g) in the form of an oil is thus obtained.

A freshly prepared 1.7N ethanolic solution of sodium ethoxide (33.5 cc) is added to 2-{3-(thieno[2,3-b]thien-2-yl)carbonyl-phenyl}propionic acid (20 g) dissolved in absolute ethanol (100 cc). After cooling for 1 hour at 4° C., the resulting crystals are filtered off, washed twice with iced absolute ethanol (total 40 cc), and dried under reduced pressure (20 mm Hg) at a temperature of about 20° C. in the presence of potassium hydroxide pellets. The sodium salt of 2-{3-(thieno[2,3-b]thien-2-yl)carbonyl-phenyl}propionic acid (15 g), melting at 298° C., is thus obtained.

2-{3-(5-Carboxy-thieno[2,3-b]thien-2-yl)carbonyl-phenyl}propionic acid can be prepared in the following way:

Methyl 2-{3-(5-methoxycarbonyl-thieno[2,3-b]thien-2-yl)carbonyl-phenyl}propionate (36 g) in solution in a mixture of potassium hydroxide pellets (26.4 g), distilled water (160 cc) and ethanol (400 cc), is stirred for 17 hours at a temperature of about 20° C. The resulting suspension is diluted with distilled water (800 cc) and filtered. The filtrate is stirred with decolourizing charcoal (3 g) and filtered. The solution obtained is added dropwise to a 5N aqueous solution of hydrogen chloride (400 cc) cooled in an ice bath, the rate of addition being regulated in such a way that the temperature of the mixture remains below 10° C. The reaction mixture is stirred for a further hour in the ice bath, and then the resulting crystals are filtered off, washed three times with distilled water (total 150 cc), and dried in air. Crude 2-{3-(5-carboxy-thieno[2,3-b]thien-2-yl)carbonylphenyl}propionic acid (24.3 g), melting at 244° C., is thus obtained.

This product is dissolved in boiling methanol (600 cc) and decolouring charcoal (5 g) is added. After filtration whilst hot, the filtrate is cooled to about 20° C., with stirring, and then cooled at 4° C. for 1 hour. The resulting crystals are filtered off, washed twice with iced methanol (total 40 cc) and dried under reduced pressure (20 mm Hg) at a temperature of about 20° C., in the presence of potassium hydroxide pellets. 2-{3-(5-Carboxy-thieno-[2,3-b]thien-2-yl)carbonyl-phenyl}propionic acid (12.3 g), melting at 248° C., is thus obtained.

After concentration of the crystallization mother liquors to half their volume, cooling, removal of the resulting crystals, and washing and drying, a further quantity (5.2 g) of said product, but melting at 247° C., is obtained.

Methyl 2-{3-(5-methoxycarbonyl-thieno[2,3-b]thien-2-yl)carbonyl-phenyl}propionate can be prepared in the following way:

2-{3-(5-Methoxycarbonyl-thieno[2,3-b]thien-2-yl)carbonyl-phenyl}propionitrile (46 g) is dissolved in a mixture of methanol (280 cc) and methylene chloride (550 cc). This solution, cooled in an ice bath, is saturated with hydrogen chloride by bubbling through a brisk stream of anhydrous hydrogen chloride for 2½ hours, and is then kept at 4° C. for 17 hours. Distilled water (500 cc) is then added to the reaction mixture which is heated progressively, whilst distilling the methylene chloride, until the temperature of the mixture reaches 70° C., a temperature which is maintained for 30 minutes. After cooling, the mixture is extracted three times with methylene chloride (total 600 cc). The combined methylene chloride extracts are washed twice with distilled water (total 200 cc), dried over anhydrous sodium sulphate and evaporated. The oily residue (50 g) obtained is immediately redissolved in boiling methanol (150 cc). After cooling, starting the crystallization and standing for 2 hours at 4° C., the resulting crystals are filtered off, washed twice with ice methanol (total 50 cc) and dried under reduced pressure (20 mm Hg) at a temperature of about 20° C. in the presence of potassium hydroxide pellets. Methyl 2-{3-(5-methoxycarbonyl-thieno[2,3-b]thien-2-yl)carbonyl-phenyl}propionate (40 g), melting at 122° C., is thus obtained.

2-{3-(5-Methoxycarbonyl-thieno[2,3-b]thien-2-yl)carbonyl-phenyl}propionitrile can be prepared in the following way:

Anhydrous aluminium chloride (134 g) is added in small portions, over a period of 1½ hours, to a mixture of methyl (thieno[2,3-b]thiophene)-2-carboxylate (39.6 g) and 2-(3-chloroformyl-phenyl)propionitrile (38.7 g) in methylene chloride (1000 cc) at about 20° C. The reaction mixture is stirred for 17 hours at a temperature of about 20° C. and then hydrolysed, with care, by the addition of an N aqueous solution of hydrogen chloride (500 cc) over a period of 2 hours, the internal temperature being held at about 20° C. by external cooling with a bath of cold water. The methylene chloride solution is decanted off, washed twice with distilled water (total 1000 cc), dried over sodium sulphate in the presence of decolourizing charcoal (10 g), filtered and evaporated. The residue is dissolved in boiling acetonitrile (125 cc). After cooling, starting the crystallization and standing for two hours at 4° C., the resulting crystals are filtered off, washed twice with iced acetonitrile (total 100 cc) and dried under reduced pressure (20 mm Hg) at a temperature of about 20° C. in the presence of potassium hydroxide pellets. 2-{3-(5-Methoxycarbonyl-thieno[2,3-b]thien-2-yl)carbonyl-phenyl}propionitrile (46 g), melting at 163° C., is thus obtained.

2-(3-Chloroformyl-phenyl)propionitrile can be prepared according to the method described in Belgian Patent Specification No. 792218.

Methyl (thieno[2,3-b]thiophene)-2-carboxylate can be prepared in the following way:

A brisk stream of anhydrous hydrogen chloride is passed into a suspension of (thieno[2,3-b]thiophene)-2-carboxylic acid (100 g) in methanol (1360 cc). The mixture is progressively heated, for about 1 hour, to boiling point. The boiling, and the passage of the stream of hydrogen chloride is maintained for 6 hours, and then the reaction mixture is concentrated to half its volume by distillation of the methanol under reduced pressure (40 mm Hg). The residue is poured into distilled water (2000 cc) and extracted four times with methylene chloride (total 1000 cc). The combined methylene chloride phases are dried over anhydrous sodium sulphate, stirred with decolourizing charcoal (3 g), filtered and evaporated. The residue (131.5 g) is dissolved in boiling diisopropyl ether (500 cc) and held at the boil for 1 hour with decolourizing charcoal (1 g). After filtering whilst hot, the solution is cooled for 1 hour at 4° C. The resulting crystals are filtered off, washed twice with iced diisopropyl ether (total 100 cc) and dried under reduced pressure (20 mm Hg) at a temperature of about 20° C. A product (57.8 g), melting at 101° C., is thus obtained and is dissolved in boiling methanol (400 cc). The solution is cooled for 1 hour at 4° C. The resulting crystals are filtered off, washed twice with iced methanol (total 100 cc) and dried under reduced pressure (20 mm Hg) at a temperature of about 20° C. in the presence of potassium hydroxide pellets. Methyl (thieno[2,3-b]thiophene)-2-carboxylate (50 g), melting at 107° C., is thus obtained.

EXAMPLE 4

2-{3-(5-Carboxy-thieno[2,3-b]thien-2-yl)carbonyl-phenyl}butyric acid (15.6 g) and copper powder (1 g) are suspended in quinoline (150 cc) and heated at 195°–200° C. for 20 minutes, and then at the boil for 10 minutes. After cooling, ice (300 g) and a 12N concentrated aqueous solution of hydrogen chloride (100 cc) are added to the reaction mixture, which is extracted three times with methylene chloride (total 600 cc). The combined methylene chloride solutions are washed three times with distilled water (total 300 cc), and then extracted twice with a 2N aqueous solution of sodium hydroxide (total 400 cc) and three times with distilled water (total 600 cc). The combined aqueous alkaline phases are acidified to pH 1 by the addition of a 12N concentrated aqueous solution of hydrogen chloride and extracted three times with methylene chloride (total 450 cc). The combined methylene chloride solutions are washed three times with distilled water (total 300 cc), dried over anhydrous sodium sulphate in the presence of decolourizing charcoal (5 g), filtered and evaporated. The residue obtained (9.3 g) is dissolved in boiling acetonitrile (70 cc). After cooling, starting the crystallization and standing for 1 hour at 4° C., the resulting crystals are filtered off, washed once with iced acetonitrile (15 cc) and dried under reduced pressure (20 mm Hg) at a temperature of about 20° C., in the presence of potassium hydroxide pellets. Crude 2-{3-(thieno[2,3-b]thien-2-yl)carbonyl-phenyl}butyric acid (7.8 g), melting at 143° C., is thus obtained.

Crude 2-{3-(thieno[2,3-b]thien-2-yl)carbonyl-phenyl}butyric acid (9 g) is dissolved in boiling acetonitrile (80 cc) to which decolourizing charcoal (0.8 g) has been added. After filtering whilst hot, the filtrate is cooled, with stirring, to about 20° C. and then cooled at 4° C. for 2 hours. The resulting crystals are filtered off, washed with iced acetonitrile (20 cc) and dried under reduced pressure (20 mm Hg) at a temperature of about 20° C. in the presence of potassium hydroxide pellets. 2-{3-(Thieno[2,3-b]thien-2-yl)carbonyl-phenyl}butyric acid (7.8 g), melting at 147° C., is thus obtained.

2-{3-(5-Carboxy-thieno[2,3-b]thien-2-yl)carbonyl-phenyl}butyric acid can be prepared in the following way:

Methyl 2-{3-(5-methoxycarbonyl-thieno[2,3-b]thien-2-yl)carbonyl-phenyl}butyrate (19.1 g), suspended in a mixture of potassium hydroxide pellets (16.6 g), distilled water (75 cc) and ethanol (200 cc), is stirred for 48 hours at a temperature of about 20° C. The resulting solution is diluted with distilled water (300 cc), washed three times with diethyl ether (total 600 cc), decolourizing charcoal (3 g) is added, and the solution is filtered and added dropwise to a 5N aqueous solution of hydrogen chloride (100 cc) cooled in an ice bath, the rate of addition being regulated in such a way that the temperature of the mixture remains below 10° C. The resulting crystals are filtered off, washed three times with distilled water (total 150 cc) and dried under reduced pressure (20 mm Hg) at a temperature of about 20° C. in the presence of potassium hydroxide pellets. 2-{3-(5-Carboxy-thieno[2,3-b]thien-2-yl)carbonyl-phenyl}butyric acid (15.8 g), melting at 240° C., is obtained.

Methyl 2-{3-(5-methoxycarbonyl-thieno[2,3-b]thien-2-yl)carbonyl-phenyl}butyrate can be prepared in the following way:

2-{3-(5-Methoxycarbonyl-thieno[2,3-b]thien-2-yl)carbonyl-phenyl}butyronitrile (20 g) is dissolved in a mixture of methylene chloride (300 cc) and methanol (150 cc). The solution, cooled by an ice bath, is saturated by bubbling through a brisk stream of anhydrous hydrogen chloride for 4 hours, and is then held at 4° C. for 2 hours. The reaction mixture, to which distilled water (350 cc) is added, is then progressively heated, whilst distilling the methylene chloride, until the temperature of the mixture reaches 65° C., a temperature which is maintained for 1 hour. After cooling, the resulting crystals are filtered off, washed twice with iced methanol (total 50 cc) and dried under reduced pressure (20 mm Hg) at a temperature of about 20° C. in the presence of potassium hydroxide pellets. Methyl 2-{3-(5-methoxycarbonyl-thieno[2,3-b]thien-2-yl)carbonyl-phenyl}butyrate (19.1 g), melting at 143° C., is thus obtained.

2-{3-(5-Methoxycarbonyl-thieno[2,3-b]thien-2-yl)carbonyl-phenyl}butyronitrile can be prepared in the following way:

Anhydrous aluminium chloride (53.5 g) is added in small portions, over a period of 1 hour, to a mixture of methyl (thieno[2,3-b]thiophene)-2-carboxylate (15.6 g) and 2-(3-chloroformyl-phenyl)butyronitrile (16.3 g) in methylene chloride (400 cc) at about 20° C. The reaction mixture is stirred for 5 hours at a temperature of about 20° C., and then poured onto crushed ice (600 g), to which has been added a 12N concentrated aqueous solution of hydrogen chloride (50 cc). The aqueous phase, after decantation, is extracted twice with methylene chloride (total 600 cc). The combined methylene chloride solutions are washed three times with distilled water (total 900 cc), dried over anhydrous sodium sulphate, filtered and evaporated. The residue obtained is dissolved in boiling acetonitrile (100 cc). After cooling, starting the crystallization and standing for 1 hour at 4° C., the resulting crystals are filtered off, washed twice with iced acetonitrile (total 30 cc) and dried under reduced pressure (20 mm Hg) at a temperature of about 20° C. in the presence of potassimm hydroxide pellets. 2-{3-(5-Methoxycarbonyl-thieno[2,3-b]thien-2-yl)carbonyl-phenyl}butyronitrile (20 g), melting at 130° C., is thus obtained.

2-(3-Chloroformyl-phenyl)butyronitrile (25.7 g), b.p. 145° C./1 mm Hg, can be obtained from crude 2-(3-carboxy-phenyl)butyronitrile (57 g) according to the method described in Belgian Patent Specification No. 792218 for 2-(3-chloroformyl-phenyl)propionitrile.

Crude 2-(3-carboxy-phenyl)butyronitrile (57 g), melting at 104° C., can be obtained from sodium 2-chlorobenzoate (115 g) and butyronitrile (138 g) according to the method described by E. R. Biehl, J. Org. Chem., 31, 602 (1966).

EXAMPLE 5

2-{3-(5-Carboxy-thieno[2,3-b]thien-2-yl)carbonyl-phenyl}hexanoic acid (12.5 g) and copper powder (1 g) are suspended in quinoline (100 cc) and heated at 165° C. for 35 minutes. The reaction mixture is then heated to 190° C. over a period of 10 minutes, then cooled, poured into a mixture of 12N concentrated aqueous hydrochloric acid (120 cc) and distilled water (400 cc), and extracted three times with methylene chloride (total 300 cc). The combined methylene chloride phases are washed twice with a 2N aqueous solution of hydrogen chloride (total 60 cc), then three times with distilled water (total 90 cc), dried over anhydrous sodium sulphate in the presence of decolourizing charcoal (0.5 g), filtered and evaporated. Crude 2-{3-(thieno[2,3-b]thien-2-yl)carbonyl-phenyl}hexanoic acid (11.8 g) is thus obtained.

Crude 2-{3-(thieno[2,3-b]thien-2-yl)carbonyl-phenyl}hexanoic acid (22.8 g) is dissolved, at 50° C., in a solution of ethanolamine (4 cc) in distilled water (140 cc). After cooling, the turbid solution is stirred with decolourizing charcoal (2 g) and filtered. The clear filtrate is acidified to pH 1 with a 12N concentrated aqueous solution of hydrogen chloride and extracted three times with methylene chloride (total 300 cc). The combined methylene chloride phases are washed three times with a 2N aqueous solution of hydrogen chloride (total 150 cc), then five times with distilled water (total 250 cc), dried over anhydrous sodium sulphate in the presence of decolourizing charcoal (0.5 g), filtered and evaporated. The residue (15 g) is dissolved in boiling acetonitrile (90 cc) and the solution is filtered whilst hot. After cooling for 1 hour at 4° C., the resulting crystals are filtered off, washed three times with iced acetonitrile (total 30 cc) and dried under reduced pressure (20 mm Hg) at a temperature of about 20° C. in the presence of potassium hydroxide pellets. Pure 2-{3-(thieno[2,3-b]thien-2-yl)carbonyl-phenyl}hexanoic acid (12 g), melting at 131° C., is thus obtained.

2-{3-(5-Carboxy-thieno[2,3-b]thien-2-yl)carbonyl-phenyl}hexanoic acid can be prepared in the following way:

Methyl 2-{3-(5-methoxycarbonyl-thieno[2,3-b]thien-2-yl)carbonyl-phenyl}hexanoate (29.6 g), suspended in a mixture of potassium hydroxide pellets (15.5 g), distilled water (50 cc) and ethanol (100 cc), is stirred for 17 hours at a temperature of about 20° C. The solvents are distilled off under reduced pressure (30 mm Hg) at 40°-50° C. and the residue is dissolved in distilled water (150 cc). The solution obtained is stirred with decolourizing charcoal (0.5 g), filtered and acidified to pH 1 by the addition of a 5N aqueous solution of hydrogen chloride. The resulting crystals are filtered off, washed three times with distilled water (total 150 cc) and dried under reduced pressure (20 mm Hg) at 70° C. in the presence of potassium hydroxide pellets. Crude 2-{3-(5-carboxy-thieno[2,3-b]thien-2-yl)carbonyl-phenyl}hexanoic acid (28.4 g), melting at 208° C., is thus obtained.

This acid can be purified in the following way:

Crude 2-{3-(5-carboxy-thieno[2,3-b]thien-2-yl)carbonyl-phenyl}hexanoic acid (14 g) is dissolved in acetone (200 cc). The turbid solution obtained is dried over anhydrous magnesium sulphate, filtered and evaporated. Purified 2-{3-(5-carboxy-thieno[2,3-b]thien-2-yl)carbonyl-phenyl}hexanoic acid (12.5 g), melting at 216° C., is thus obtained.

Methyl 2-{3-(5-methoxycarbonyl-thieno[2,3-b]thien-2-yl)carbonyl-phenyl}hexanoate can be prepared in the following way:

2-{3-(5-Methoxycarbonyl-thieno[2,3-b]thien-2-yl)carbonyl-phenyl}hexanenitrile (53.3 g) is dissolved in a mixture of methanol (250 cc) and methylene chloride (500 cc). The solution, after cooling to −5° C., is saturated with hydrogen chloride by bubbling through a brisk stream of anhydrous hydrogen chloride for 6 hours, and is then kept at 4° C. for 17 hours. Distilled water (400 cc) is then added to the reaction mixture, which is heated progressively, whilst distilling the methylene chloride, until the temperature of the mixture reaches 70° C., a temperature which is maintained for 2 hours. After cooling, the mixture is diluted with distilled water (700 cc) and extracted three times with methylene chloride (total 600 cc). The combined methylene chloride extracts are washed three times with distilled water (total 300 cc), dried over anhydrous sodium sulphate in the presence of decolourizing charcoal (1 g), filtered and evaporated. The residue (61 g) is dissolved in boiling methanol (120 cc). After cooling for 1 hour at 4° C., the resulting crystals are filtered off, washed three times with iced methanol (total 45 cc) and dried under reduced pressure (20 mm Hg) at a temperature of about 20° C. in the presence of potassium hydroxide pellets. Methyl 2-{3-(5-methoxycarbonyl-thieno[2,3-b]thien-2-yl)carbonyl-phenyl}hexanoate (34.7 g), melting at 95° C., is thus obtained.

2-{3-(5-Methoxycarbonyl-thieno[2,3-b]thien-2-yl)carbonyl-phenyl}hexanenitrile can be prepared in the following way:

Anhydrous aluminium chloride (106 g) is added in small portions over a period of 3 hours to a mixture of methyl (thieno[2,3-b]thiophene)-2-carboxylate (31.7 g) and 2-(3-chloroformyl-phenyl)hexanenitrile (39.5 g) in methylene chloride (800 cc) at about 20° C. The mixture is stirred for 17 hours at a temperature of about 20° C. and then hydrolysed, with care, by the addition of a 2N aqueous solution of hydrogen chloride (1000 cc), the internal temperature being held at about 10° C. by cooling externally with an ice bath. The aqueous phase is decanted off and extracted three times with methylene chloride (total 300 cc). The combined methylene chloride phases are washed three times with distilled water (total 300 cc), dried over anhydrous sodium sulphate in the presence of decolourizing charcoal (0.5 g), filtered and evaporated. The residue (64 g) is dissolved in boiling acetonitrile (150 cc) and the solution, which is stirred with decolourizing charcoal (0.5 g), is filtered and then cooled at 4° C. for 1 hour. The resulting crystals are filtered off, washed three times with iced acetonitrile (total 60 cc) and dried under reduced pressure (20 mm Hg) at a temperature of about 20° C. in the presence of potassium hydroxide pellets. 2-{3-(5-Methoxycarbonyl-thieno[2,3-b]thien-2-yl)carbonyl-phenyl}hexanenitrile (53.3 g), melting at 131° C., is thus obtained.

2-(3-Chloroformyl-phenyl)hexanenitrile (39.5 g), b.p. 151°–152° C./0.4 mm Hg, can be obtained from 2-(3-carboxy-phenyl)hexanenitrile (40 g) according to the method described in Belgian Patent Specification No. 792218 for 2-(3-chloroformyl-phenyl)propionitrile.

2-(3-Carboxy-phenyl)hexanenitrile (75 g), melting at 136° C., can be obtained from sodium 2-chlorobenzoate (115 g) and hexanenitrile (194 g) according to the method described by E. R. Biehl, J. Org. Chem., 31, 602 (1966).

EXAMPLE 6

Ethyl 2-{4-(thieno[2,3-b]thien-2-yl)carbonyl-phenyl}-2-methyl-malonate (16.23 g) is suspended in a mixture of 5% (w/v) aqueous sodium hydroxide solution (90 cc) and ethanol (90 cc), and the suspension is heated at the boiling point for 3 hours. After cooling, the reaction mixture is diluted with distilled water (1000 cc), and then extracted three times with diethyl ether (total 600 cc). The aqueous phase is filtered off, acidified to pH 1 by the addition of a 5N aqueous hydrochloric acid solution and extracted three times with diethyl ether (total 600 cc). The combined ether solutions are washed three times with distilled water (total 300 cc), dried over anhydrous sodium sulphate, decolourizing charcoal (1 g) is added, and the solutions are filtered and evaporated. Crude 2-{4-(thieno[2,3-b]thien-2-yl)carbonyl-phenyl}propionic acid (9.9 g), melting at 150° C., is thus obtained.

Crude 2-{4-(thieno[2,3-b]thien-2-yl)carbonyl-phenyl}propionic acid (12.7 g), obtained under the conditions described above, is dissolved in boiling acetonitrile (60 cc), to which decolourizing charcoal (0.2 g) has been added. After filtering whilst hot, the filtrate is cooled, with stirring, to about 20° C. and then kept at 4° C. for 48 hours. The resulting crystals are filtered off, washed three times with iced acetonitrile (total 15 cc) and dried under reduced pressure (20 mm Hg) at a temperature of about 20° C. in the presence of potassium hydroxide pellets. 2-{4-(Thieno[2,3-b]thien-2-yl)carbonyl-phenyl}propionic acid (10.6 g), melting at 150° C., is thus obtained.

Ethyl 2-{4-(thieno[2,3-b]thien-2-yl)carbonyl-phenyl}-2-methyl-malonate can be prepared in the following way:

A 50% dispersion in mineral oil of sodium hydride (6.2 g), previously washed with cyclohexane, is suspended in distilled hexamethylphosphotriamide (472 cc) and ethyl methylmalonate (22.6 g) is added dropwise. The reaction mixture is stirred at a temperature of about 20° C. until the evolution of hydrogen has ceased, then cooled to 10° C. and purged by the passing through of a stream of dry nitrogen. (4-Fluorophenyl) (thieno[2,3-b]thien-2-yl)ketone (30.9 g) is added and the reaction mixture is heated at 100° C. for 10 hours. After cooling, the reaction mixture is diluted with toluene (945 cc) and washed with an aqueous saturated sodium chloride solution (4700 cc). The aqueous phase is extracted three times with toluene (total 1400 cc). The combined toluene solutions are washed three times with distilled water (total 1400 cc), dried over anhydrous sodium sulphate, decolourizing charcoal (1 g) is added, and the solutions are filtered and evaporated. Crude ethyl 2-{4-(thieno[2,3-b]thien-2-yl)carbonyl-phenyl}-2-methyl-malonate (47.5 g), in the form of an oil, is thus obtained. This product is dissolved in diethyl ether (600 cc) and filtered over silica gel (300 g). The latter is washed four times with diethyl ether (total 2400 cc), and the combined ether solutions are evaporated. The residue obtained (45.9 g) is chromatographed on a column (4.2 cm diameter, 42 cm height) containing silica gel (300 g). Successive elutions are carried out with cyclohexane (1200 cc), a mixture (600 cc) of ethyl acetate (6 cc) and cyclohexane (594 cc), a mixture (600 cc) of ethyl acetate (12 cc) and cyclohexane (588 cc), a mixture (600 cc) of ethyl acetate (24 cc) and cyclohexane (576 cc) and a mixture (1700 cc) of ethyl acetate (136 cc) and cyclohexane (1564 cc).

All the corresponding eluates are discarded. Elution is then carried out with a mixture (2400 cc) of ethyl acetate (240 cc) and cyclohexane (2160 cc). The eluate obtained is evaporated and the residue (22.6 g) is triturated in diisopropyl ether (50 cc). The resulting crystals are filtered off, washed twice with diisopropyl ether (total 50 cc) and dried under reduced pressure (20 mm Hg) at a temperature of about 20° C. in the presence of potassium hydroxide pellets. Ethyl 2-{4-(thieno[2,3-b]thien-2-yl)carbonyl-phenyl}-2-methyl-malonate (16.5 g), melting at 92° C., is thus obtained.

(4-Fluorophenyl) (thieno[2,3-b]thien-2-yl) ketone can be prepared in the following way:

5-(4-Fluorobenzoyl)-thieno[2,3-b]thiophene-2-carboxylic acid (48.1 g) and copper powder (8.2 g) are suspended in quinoline (410 cc) and heated at the boiling point for 5 minutes. After cooling, decolourizing charcoal (0.5 g) is added to the reaction mixture which is then filtered. The solution obtained is added dropwise to a mixture of distilled water (620 cc) and a 12N aqueous solution of hydrogen chloride (289 cc), cooled in an ice bath, the rate of addition being regulated in such a way that the temperature of the mixture remains below 10° C. Distilled water (500 cc) is added to the reaction mixture, which is stirred for a further 30 minutes in the ice bath, and then the resulting crystals are filtered off, washed four times with distilled water (total 2000 cc) and dried in air. Crude (4-fluorophenyl) (thieno[2,3-b]thien-2-yl) ketone (38.1 g), melting at 113° C., is thus obtained.

(4-Fluorophenyl) (thieno[2,3-b]thien-2-yl) ketone (43 g) is dissolved in boiling diisopropyl ether (900 cc) to which has been added decolourizing charcoal (0.5 g). After filtering whilst hot, the filtrate is cooled, with stirring, to about 20° C. and then kept at 4° C. for 4 hours. The resulting crystals are filtered off, washed three times with iced diisopropyl ether (total 30 cc), and dried under reduced pressure (20 mm Hg) at a temperature of about 20° C. in the presence of potassium hydroxide pellets. (4-Fluorophenyl) (thieno[2,3-b]thien-2-yl) ketone (31 g), melting at 117° C., is thus obtained.

5-(4-Fluorobenzoyl)-thieno[2,3-b]thiophene-2-carboxylic acid can be prepared in the following way:

Methyl 5-(4-fluorobenzoyl)-thieno[2,3-b]thiophene-2-carboxylate (51.7 g), suspended in a mixture of potassium hydroxide pellets (23.1 g), distilled water (260 cc) and ethanol (520 cc), is heated at the boiling point for 90 minutes. The volume of the reaction mixture is reduced to a third by distillation under reduced pressure (30 mm Hg) at 40°-50° C. 2.5N Aqueous hydrochloric acid (1000 cc) is added to the residue obtained, and the mixture is heated at the boiling point for 10 minutes. After cooling, the resulting crystals are filtered off, washed four times with distilled water (total 2000 cc) and dried in air. 5-(4-Fluorobenzoyl)-thieno[2,3-b]thiophene-2-carboxylic acid (48.1 g), subliming at 324° C., is thus obtained.

Methyl 5-(4-fluorobenzoyl)-thieno[2,3-b]thiophene-2-carboxylate can be prepared in the following way:

Anhydrous aluminium chloride (136 g) is added in small portions, over a period of 30 minutes, to a mixture of methyl thieno[2,3-b]thiophene-2-carboxylate (40.3 g) and 4-fluorobenzoyl chloride (32.3 g) in methylene chloride (1000 cc) at about 25° C. The reaction mixture is stirred for 3 hours at a temperature of about 20° C. and then hydrolysed, with care, by the addition over a period of 30 minutes of 0.5N aqueous hydrochloric acid (500 cc), the internal temperature being maintained at about 20° C. by external cooling with a bath of cold water. The methylene chloride solution is diluted with methylene chloride (5000 cc), decanted off, washed three times with distilled water (total 3000 cc), three times with a saturated aqueous sodium bicarbonate solution (total 1000 cc), and again three times with distilled water (total 3000 cc), then dried over anhydrous sodium sulphate in the presence of decolourizing charcoal (1 g), filtered and evaporated. The residue is triturated in diethyl ether (250 cc), the resulting crystals are filtered off, washed three times with diethyl ether (total 375 cc) and dried under reduced pressure (20 mm Hg) at a temperature of about 20° C. in the presence of potassium hydroxide pellets. Methyl 5-(4-fluorobenzoyl)-thieno[2,3-b]thiophene-2-carboxylate (51.8 g), melting at 220° C., is thus obtained.

4-Fluorobenzoyl chloride can be prepared according to F. Fichter and J. Rosenzweig, Helv. Chim. Acta., 16, 1156 (1933).

EXAMPLE 7

2-{3-(Thieno[3,2-b]thien-2-yl)carbonyl-phenyl}propionitrile (32.7 g), in solution in a mixture of 35% (w/v) aqueous potassium hydroxide solution (50 cc) and ethanol (200 cc) is heated at the boiling point for 6 hours, the development of the reaction being followed by the quantity of ammonia liberated. After cooling, the mixture is evaporated under reduced pressure (20 mm Hg) at 40° C. and the residue, taken up in distilled water (300 cc), is extracted three times with diethyl ether (total 150 cc). The aqueous solution is stirred with decolourizing charcoal (3 g), filtered, acidified to pH 2 by the addition of 12N aqueous hydrochloric acid and extracted four times with diethyl ether (total 280 cc). The combined ether extracts are washed three times with distilled water (total 150 cc), dried over anhydrous sodium sulphate and evaporated. The residue (23 g) is dissolved in boiling acetic acid (50 cc) and decolourizing charcoal (2 g) is added to the solution which is filtered and then stirred for 17 hours at a temperature of about 20° C. The resulting crystals are filtered off, washed with cold acetic acid (8 cc) and dried under reduced pressure (20 mm Hg) at a temperature of about 20° C. in the presence of potassium hydroxide pellets. 2-{3-Thieno[3,2-b]thien-2-yl)carbonyl-phenyl}propionic acid (9 g), melting at 133° C., is thus obtained.

2-{3-(Thieno[3,2-b]thien-2-yl)carbonyl-phenyl}propionitrile can be prepared in the following way:

A solution of thieno[3,2-b]thiophene (28 g) and 2-(3-chloroformyl-phenyl)propionitrile (56.5 g) in methylene chloride (500 cc) is added dropwise, over a period of 1 hour, to a suspension of anhydrous aluminium chloride (83.5 g) in methylene chloride (500 cc). The mixture is stirred for 17 hours at a temperature of about 20° C. and then poured onto crushed ice (1 kg). The methylene chloride solution is decanted off, washed twice with distilled water (total 600 cc), twice with a 10% (w/v) aqueous sodium carbonate solution (total 600 cc), twice with distilled water (total 600 cc), dried over anhydrous sodium sulphate and evaporated. The residue is taken up in diethyl ether (600 cc), stirred with decolourizing charcoal (5 g) and filtered. The filtrate is evaporated and the residue (60 g), dissolved in methylene chloride (200 cc), is stirred for 2 hours with an N aqueous sodium hydroxide solution. The methylene chloride phase is decanted off, washed three times with distilled water (total 300 cc), dried over anhydrous sodium sulphate and evaporated. The residue (49 g) is dissolved in a boiling mixture of ethyl acetate (40 cc) and ethanol (160 cc). After cooling for 3 hours at 4° C., the resulting crystals are filtered off, washed twice with a mixture (total 40 cc) of ethyl acetate and ethanol (20:80) and dried under reduced pressure (20 mm Hg) at a temperature of about 20° C. in the presence of potassium hydroxide pellets. 2-{3-(Thieno[3,2-b]thien-2-yl)carbonyl-phenyl}propionitrile (36.6 g), melting at 75° C., is thus obtained.

2-(3-Chloroformyl-phenyl)propionitrile can be prepared according to the method described in Belgian Patent Specification No. 792218.

Thieno[3,2-b]thiophene can be prepared according to the method of A. Bugge [Acta Chem. Scand., 22, 63 (1968)].

EXAMPLE 8

A solution of 2-diethylamino-chloroethane (1.6 g) in dimethylformamide (16 cc) is added dropwise to a suspension of sodium 2-{3-(thieno[2,3-b]thien-2-yl)carbonyl-phenyl}propionate (4 g) [prepared as described in Example 1] in dimethylformamide (16 cc). After 16 hours at 25° C., the reaction mixture is poured into distilled water (400 cc) and extracted three times with diethyl ether (total 300 cc). The combined ether phases are washed with a saturated aqueous sodium bicarbonate solution (75 cc), then three times with distilled water (total 300 cc), dried over anhydrous sodium sulphate in the presence of decolourizing charcoal (0.5 g), filtered and evaporated. The residue obtained (4.75 g), to which is added some product (3.1 g) prepared in the same way, is dissolved in 1N aqueous hydrochloric acid (50 cc). The solution is washed three times with diethyl ether (total 175 cc) and then rendered alkaline to pH 11 by the addition of 1N aqueous sodium hydroxide solution (55 cc). The resulting precipitate is extracted three times with diethyl ether (175 cc). The combined ether solutions are washed three times with distilled water (total 175 cc), dried over anhydrous sodium sulphate in the presence of decolourizing charcoal (0.5 g), filtered and evaporated. 2-Diethylaminoethyl 2-{3-(thieno[2,3-b]thien-2-yl)carbonyl-phenyl}propionate (5.3 g), in the form of an oil, is thus obtained.

2-Diethylaminoethyl 2-{3-(thieno[2,3-b]thien-2-yl)carbonyl-phenyl}propionate (4.3 g) is dissolved in absolute ethanol (15 cc) and a solution of anhydrous oxalic acid (0.93 g) in absolute ethanol (5 cc) is added. After 20 hours at 25° C., the resulting crystals are filtered off, washed three times with iced absolute ethanol (total 15 cc) and dried under reduced pressure (20 mm Hg) at a temperature of about 20° C. in the presence of potassium hydroxide pellets. The acid oxalate of 2-diethylaminoethyl 2-{3-(thieno[2,3-b]thien-2-yl)carbonyl-phenyl}propionate (3.9 g), melting at 120° C., is thus obtained.

EXAMPLE 9

N,N'-Carbonyldiimidazole (3.8 g) is added to 2-{3-(thieno[2,3-b]thien-2-yl)carbonyl-phenyl}propionic acid (7.25 g) [prepared as described in a previous Example] in solution in diethyl ether (70 cc). When the evolution of gas has ceased, 2-dimethylaminoethylamine (2.1 g) in solution in diethyl ether (25 cc) is then added. After 20 hours at 25° C., the reaction mixture is evaporated. The residue, dissolved in methylene chloride (100 cc), is washed four times with a 5% (w/v) aqueous sodium chloride solution (total 400 cc), dried over anhydrous sodium sulphate in the presence of decolourizing charcoal (0.5 g), filtered and evaporated. The oil obtained (5.4 g) is dissolved in N aqueous hydrochloric acid solution (50 cc). This solution is washed three times with diethyl ether (total 150 cc) and then rendered alkaline to pH 11 by the addition of 1N aqueous sodium hydroxide solution (55 cc). The resulting precipitate is extracted three times with methylene chloride (total 150 cc). The combined methylene chloride solutions are washed three times with distilled water (total 150 cc), dried over anhydrous sodium sulphate in the presence of decolourizing charcoal (0.5 g), filtered and evaporated. N-(2-Dimethylaminoethyl) 2-{3-(thieno-[2,3-b]thien-2-yl)carbonyl-phenyl}propionamide (3.3 g), in the form of an oil, is thus obtained.

N-(2-Dimethylaminoethyl) 2-{3-(thieno[2,3-b]thien-2-yl)carbonyl-phenyl}propionamide (3.8 g) is dissolved in absolute ethanol (15 cc) and a solution of anhydrous oxalic acid (0.9 g) in absolute ethanol (5 cc) is added. After 20 hours at 25° C., the resulting crystals are filtered off, washed three times with iced absolute ethanol (total 15 cc) and dried under reduced pressure (20 mm Hg) at a temperature of about 20° C. in the presence of potassium hydroxide pellets. N-(2-Dimethylaminoethyl) 2-{3-(thieno[2,3-b]thien-2-yl)carbonyl-phenyl}•propionamide acid oxalate (3.4 g), melting at 160° C., is thus obtained.

The present invention includes within its scope pharmaceutical compositions which comprise, as active ingredient, at least one of the compounds of general formula I, or — when appropriate — a pharmaceutically acceptable salt thereof, in association with a pharmaceutical carrier or coating. The invention includes especially such preparations made up for oral, parenteral or rectal administration, or as ointments.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening flavouring and aromatizing agents. The compositions according to the invention, for oral administration also include capsules of absorbable material such as gelatin containing the active substance with or without the addition of diluents or excipients.

Compositions according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

In human therapy the compositions can be used, in particular, in the treatment of rheumatic or traumatic aches, dental or visceral pains, various aches (pains from cancers), febrile states, and medical, surgical and obstretrical emboligenic and thrombogenic conditions.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. In human therapy the compositions when administered orally to an adult should generally give doses between 150 mg and 2000 mg of active substance per day. In general the physician will decide the posology considered appropriate, taking into account the age and weight and other factors intrinsic to the patient being treated.

The following Example illustrates pharmaceutical compositions according to the present invention.

EXAMPLE 10

Tablets weighing 500 mg and having the following composition are prepared in accordance with the usual technique:

| | |
|---|---|
| 2-{3-(thieno[3,2-b]thien-2-yl)carbonyl-phenyl}-propionic acid | 250 mg |
| starch | 190 mg |
| colloidal silica | 50 mg |
| magnesium stearate | 10 mg. |

We claim:

1. A thienothienylcarbonyl-phenylalkanoic acid compound of the formula:

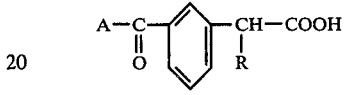

(wherein R represents hydrogen or an alkyl radical, $R_1$ represents a hydroxy, amino or alkoxy radical, or an alkylamino or dialkylamino group; the various alkyl radicals and the alkoxy radical being optionally substituted by a dialkylamino group, it being understood that in the definitions of R and $R_1$ above the alkyl radicals and the alkoxy radical contain from 1 to 4 carbon atoms, and the symbol A represents the thieno[2,3-b]thien-2-yl or thieno[3,2-b]thien-2-yl radical, the A—CO— grouping being attached to the 3- or 4-position of the phenyl ring), and when $R_1$ represents the hydroxy radical its pharmaceutically acceptable metal salts, ammonium salt and addition salts with nitrogen-containing bases, and when $R_1$ represents a group containing basic nitrogen its pharmaceutically acceptable acid addition salts.

2. A compound according to claim 1 wherein R represents hydrogen or an alkyl radical containing from 1 to 4 carbon atoms; $R_1$ represents the hydroxy radical, and A represents the thieno[2,3-b]thien-2-yl radical, the A—CO— grouping being attached to the 3- or 4-position of the phenyl ring, and its pharmaceutically acceptable metal salts, ammonium salt and addition salts with nitrogen-containing bases.

3. A compound according to claim 1 wherein R and $R_1$ are as defined in claim 1, and A represents the thieno[3,2-b]thien-2-yl radical, the A—CO— grouping being attached to the 3- or 4-position of the phenyl ring, and when $R_1$ represents the hydroxy radical its pharmaceutically acceptable metal salts, ammonium salt and addition salts with nitrogen-containing bases, and when $R_1$ represents a group containing basic nitrogen its pharmaceutically acceptable acid addition salts.

4. A compound according to claim 1 wherein R and A are as defined in claim 1, and $R_1$ represents the hydroxy radical, or an alkoxy radical substituted by a dialkylamino group, or an alkylamino group substituted on the alkyl radical by a dialkylamino group, the said alkoxy radical and alkyl radicals containing 1 to 4 carbon atoms, and when $R_1$ represents the hydroxy radical its pharmaceutically acceptable metal salts, ammonium salt and addition salts with nitrogen-containing bases, and when $R_1$ is other than the hydroxy radical its pharmaceutically acceptable acid addition salts.

5. A compound according to claim 1 of the formula:

wherein R and A are as defined in claim 1, and its pharmaceutically acceptable metal salts, ammonium salt, and addition salts with nitrogen-containing bases.

6. A compound according to claim 1 which is 2-{3-(thieno[2,3-b]thien-2-yl)carbonyl-phenyl}propionic acid and its pharmaceutically acceptable metal salts, ammonium salt, and addition salts with nitrogen-containing bases.

7. A compound according to claim 1 which is 3-(thieno[2,3-b]thien-2-yl)carbonyl-phenylacetic acid and its pharmaceutically acceptable metal salts, ammonium salt, and addition salts with nitrogen-containing bases.

8. A compound according to claim 1 which is 2-{3-(thieno[2,3-b]thien-2-yl)carbonyl-phenyl}butyric acid and its pharmaceutically acceptable metal salts, ammonium salt, and addition salts with nitrogen-containing bases.

9. A compound according to claim 1 which is 2-{3-(thieno[2,3-b]thien-2-yl)carbonyl-phenyl}hexanoic acid and its pharmaceutically acceptable metal salts, ammonium salt, and addition salts with nitrogen-containing bases.

10. A compound according to claim 1 which is 2-{4-(thieno[2,3-b]thien-2-yl)carbonyl-phenyl}propionic acid and its pharmaceutically acceptable metal salts, ammonium salt, and addition salts with nitrogen-containing bases.

11. A compound according to claim 1 which is 2-{3-(thieno[3,2-b]thien-2-yl)carbonyl-phenyl}propionic acid and its pharmaceutically acceptable metal salts ammonium salts, and addition salts with nitrogen-containing bases.

12. A compound according to claim 1 which is 2-diethylaminoethyl 2-{3-(thieno[2,3-b]thien-2-yl)carbonyl-phenyl)propionate and its pharmaceutical acceptable acid addition salts.

13. A compound according to claim 1 which is N(2-dimethylaminoethyl) 2-{3-(thieno[2,3-b]thien-2-yl-carbonyl-phenyl}propionamide and its pharmaceutically acceptable acid addition salts.

* * * * *